US012685612B2

(12) United States Patent
Lenzenhuber et al.

(10) Patent No.: US 12,685,612 B2
(45) Date of Patent: Jul. 21, 2026

(54) MODULAR DETECTION SYSTEM FOR STERILE CIRCUIT MONITORING AND METHOD FOR MONITORING A STERILE MATERIAL CIRCUIT

(71) Applicant: Aesculap AG, Tuttlingen (DE)

(72) Inventors: Frederick Lenzenhuber, Tuttlingen (DE); Lukas Boehler, Furtwangen (DE); Daniol Mateusz, Kozlow (PL); Roland-Alois Hoegerle, Tuttlingen (DE); Stephanie Auber, Tuttlingen (DE); Ralf Pfister, Trossingen (DE)

(73) Assignee: Aesculap AG, Tuttlingen (DE)

( * ) Notice: Subject to any disclaimer, the term of this patent is extended or adjusted under 35 U.S.C. 154(b) by 553 days.

(21) Appl. No.: 18/028,322

(22) PCT Filed: Sep. 20, 2021

(86) PCT No.: PCT/EP2021/075773
§ 371 (c)(1),
(2) Date: Mar. 24, 2023

(87) PCT Pub. No.: WO2022/063718
PCT Pub. Date: Mar. 31, 2022

(65) Prior Publication Data
US 2023/0372057 A1 Nov. 23, 2023

(30) Foreign Application Priority Data
Sep. 25, 2020 (DE) ..................... 10 2020 125 114.9

(51) Int. Cl.
*A61B 90/98* (2016.01)
*A61B 50/34* (2016.01)
(Continued)

(52) U.S. Cl.
CPC .............. *A61B 90/98* (2016.02); *A61B 50/34* (2016.02); *A61L 2/24* (2013.01); *G16H 40/40* (2018.01); *A61L 2202/14* (2013.01)

(58) Field of Classification Search
CPC ......... A61B 90/98; A61B 50/34; A61B 90/90; A61L 2/24; A61L 2202/14; A61L 2/26;
(Continued)

(56) References Cited

U.S. PATENT DOCUMENTS

2007/0094303 A1 4/2007 Zwingenberger et al.
2007/0202005 A1* 8/2007 Maschke ............... G16H 40/40
422/62
(Continued)

FOREIGN PATENT DOCUMENTS

CN 111512389 A 8/2020
DE 102011050333 A1 11/2012
(Continued)

OTHER PUBLICATIONS

Office Action received in Japanese Application No. 2023-519097 dated Aug. 29, 2023, with translation, 9 pages.
(Continued)

*Primary Examiner* — James J Yang
(74) *Attorney, Agent, or Firm* — Christopher A. Rothe; CM Law

(57) ABSTRACT

A modular detection system for insertion in a strainer basket for detecting, monitoring and tracing sterile material in a sterilization circuit. The modular detection system includes a strainer basket insert which can be inserted directly in the strainer basket or arranged on a base plate. The system further includes the following individually and optionally electrically coupleable modules: a central electronic unit, a defined or freely selectable number of slots for attaching and/or connecting a predetermined number of retainer sys-
(Continued)

tems for retaining sterile material, each retainer system having at least one antenna system for reading a transponder in the sterile material. The system further includes a preferably defined number of conductor tracks to electrically connect the slots and/or retaining systems to one another and/or to the central electronic unit.

11 Claims, 5 Drawing Sheets

(51) Int. Cl.
  *A61L 2/24* (2006.01)
  *G16H 40/40* (2018.01)

(58) Field of Classification Search
  CPC ........ G16H 40/40; G16H 40/20; G16H 40/63;
                                    G06K 19/07749
  See application file for complete search history.

(56) References Cited

U.S. PATENT DOCUMENTS

| | | |
|---|---|---|
| 2007/0296596 A1 | 12/2007 | Moore |
| 2008/0142605 A1 | 6/2008 | Butsch |
| 2010/0252626 A1 | 10/2010 | Elizondo et al. |
| 2014/0085052 A1 | 3/2014 | Singh et al. |
| 2015/0115029 A1 | 4/2015 | Rahim et al. |
| 2015/0282701 A1 | 10/2015 | Oskin et al. |
| 2017/0224859 A1 | 8/2017 | Broninx et al. |
| 2018/0153639 A1* | 6/2018 | Wehrle ............... G06K 19/0717 |
| 2019/0104919 A1 | 4/2019 | Shelton, IV et al. |

| | | |
|---|---|---|
| 2019/0122013 A1 | 4/2019 | Hussain et al. |
| 2020/0085427 A1 | 3/2020 | Giordano et al. |
| 2021/0007822 A1* | 1/2021 | Pruckner ............... A61B 50/33 |

FOREIGN PATENT DOCUMENTS

| | | |
|---|---|---|
| DE | 102015108264 A1 | 12/2016 |
| EP | 2416298 A2 | 2/2012 |
| EP | 2914195 B1 | 12/2019 |
| JP | 2008173462 A | 7/2008 |
| JP | 2016516643 A | 6/2016 |
| JP | 2017518088 A | 7/2017 |
| JP | 2017534429 A | 11/2017 |
| WO | 2009003231 A1 | 1/2009 |
| WO | 2014159624 A1 | 10/2014 |
| WO | 2019067539 A1 | 4/2019 |

OTHER PUBLICATIONS

Office Action received in Chinese Application No. 202180064634.1 dated Mar. 14, 2024, with translation, 8 pages.
Search Report received in German Application No. 10 2020 125 114.9 dated Sep. 6, 2021, with translation, 19 pages.
Search Report received in International Application No. PCT/ EP2021/075773 dated Dec. 20, 2021, with translation, 5 pages.
Written Opinion received in International Application No. PCT/ EP2021/075773 dated Dec. 20, 2021, with translation, 11 pages.
Search Report received in Chinese Application No. 202180064634.1 dated Dec. 5, 2023, with translation, 5 pages.
English Translation of "First Notice of Examination Action" in Chinese Application No. 202180064634.1 dated Dec. 6, 2023, 6 pages.

* cited by examiner

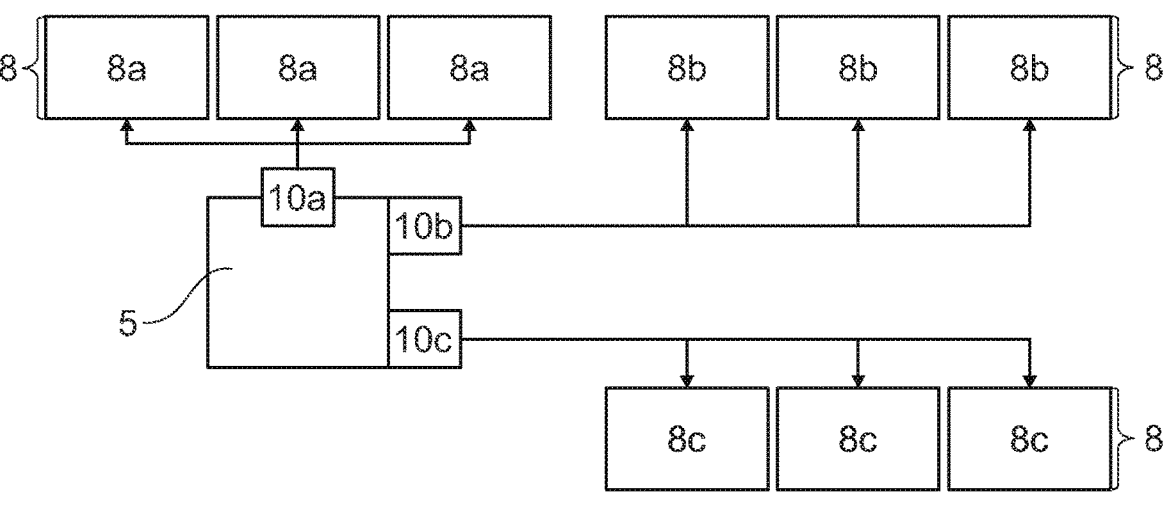
Fig. 17
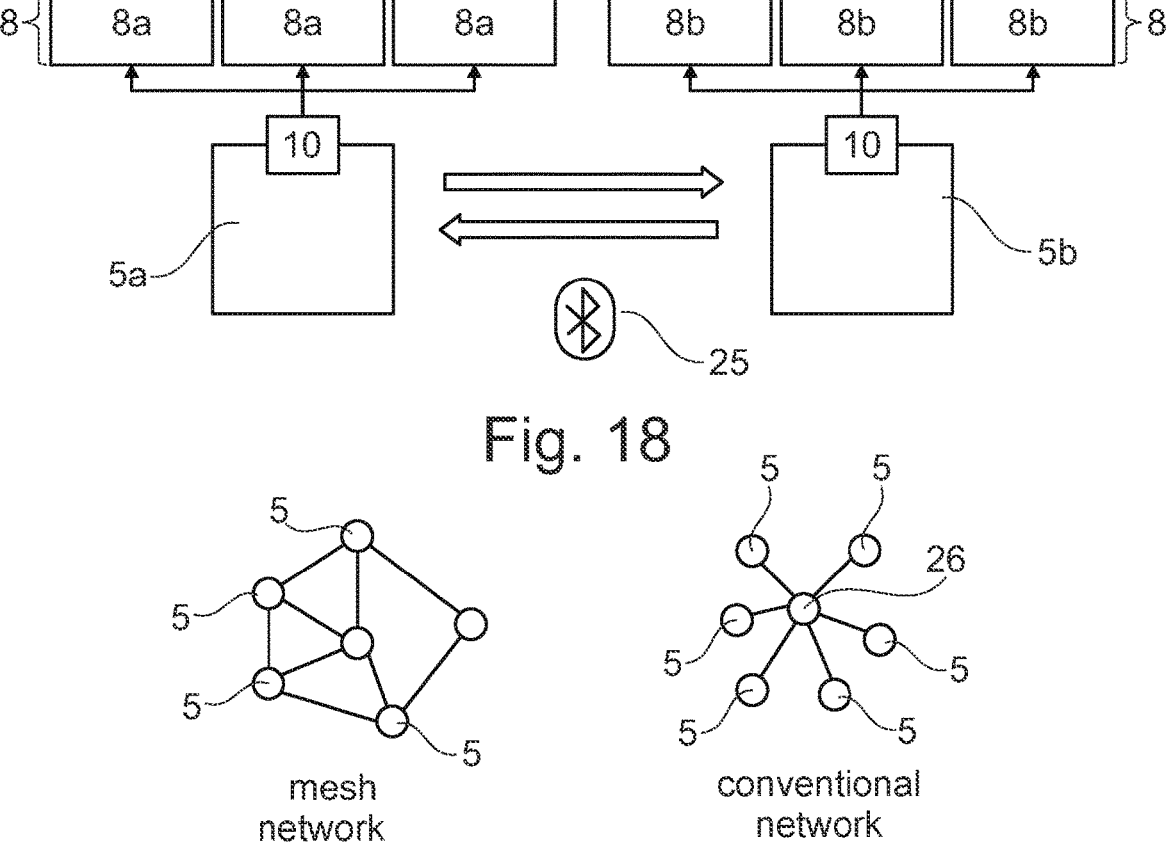
Fig. 18
mesh
network
conventional
network
Fig. 19

MODULAR DETECTION SYSTEM FOR STERILE CIRCUIT MONITORING AND METHOD FOR MONITORING A STERILE MATERIAL CIRCUIT

CROSS-REFERENCE TO RELATED APPLICATIONS

This application is the United States national phase entry of International Application No. PCT/EP2021/075773, filed Sep. 20, 2021, and claims priority to German Application No. 10 2020 125 114.9, filed Sep. 25, 2020. The contents of International Application No. PCT/EP2021/075773 and German Application No. 10 2020 125 114.9 are incorporated by reference herein in their entireties.

FIELD

The present disclosure relates to a modular detection system for insertion into a sieve basket for detecting, monitoring and tracing sterile goods, a retainer system, a sieve basket system as well as a method for monitoring a sterile goods cycles comprising at least one modular detection system.

BACKGROUND

For the monitoring and traceability of sterile goods, it has to be possible to determine whether medical/surgical instruments and/or apparatuses/devices and/or motor systems and/ or medical products have successfully undergone the entire reprocessing process and all necessary maintenance steps have been carried out. The problem arises here that sensors can only be housed in larger sterile goods and therefore, in particular for medical/surgical instruments, there is no possibility of monitoring. Another problem is the connection of smart retainer systems, i.e. of holders with sensor electronics, in a sieve basket which is not specially designed for this purpose.

Retainer devices of the present type are provided, among other things, for cleaning and holding motors, handpieces, surgical instruments and medical products in general. The retainers are arranged/used/employed with medical products arranged in the retainers in medical cleaning facilities, in particular sterilizers, cleaning and disinfection facilities (WD, rinsing facilities) or the like. In addition, it is also possible for the retainers to be used together with sterile containers or soft packaging and to be arranged within these, so that after sterilization of the medical products it is ensured that renewed contamination of the medical products is effectively prevented.

The prior art describes retainer systems for medical motor systems equipped with sensors, a communication module and a data processing unit. In this context, US 2008/142 605 A1 shows a marking device for a storage and/or transport container for medical devices with a mat of sterilizable material and a marking element for storing electronic information about characteristic parameters of the medical devices and transport containers stored and/or transported in the storage, which can be read wirelessly, wherein an RFID tag is used, for example, as a marking element in which information about sterilization processes, sterilization time and/or other parameters characteristic of the medical devices housed in the storage and/or transport container is stored.

DE 10 2011 050 333 A1 relates to a surgical container detection system, with which the contents of a sterilization container can be easily and reliably determined, comprising a container content sensor device for arrangement in or on a sterilization container, wherein the container content sensor device comprises a carrier and at least one sensor arranged or formed on the carrier for detecting an identification element which is arranged or formed on an item stored in a sterilization container for identification thereof.

EP 2 416 298 A4 discloses a portable container inventory control system that uses RFID technology to automatically monitor the removal and return of items such as tools, weapons, jewelry, surgical instruments from one or more containers in a portable container in order to maintain the status of each element and an operational record of each element.

EP 2 914 195 B1 relates to various systems and methods for marking and tracking surgical devices/instruments using RFID tags that enable tracking of surgical devices during their distribution and sterilization. In one embodiment, the system includes a tray configured to hold a plurality of surgical devices, and to which a superordinate RFID tag is attached that contains and/or facilitates access to information about the tray and about each of the surgical devices seated therein. Each of the surgical devices seated within the instrument tray may have a subordinate RFID tag attached thereto that contains information and/or facilitates access to information about the surgical device.

WO 2009/003231 A1 describes a system for identifying items undergoing sterilization, comprising a container for holding items provided with RFID tags that can withstand a sterilization process. The container has one or more internal antennas. The system also includes a container interrogator/ interrogation device for inquiring the item tags via the internal antennas of the container, wherein the interrogator/ interrogation device is removably coupled to the container.

DE 10 2015 108 264 A1 describes a surgical or medical container content detection system having a container content sensor means for placement in a sterilization container, wherein the container content sensor means comprises a carrier and at least one sensor disposed or formed on the carrier for detecting at least one identifying element disposed or formed on an item stored in the sterilization container for identification thereof. A carrier module arranged on the carrier has a detection device for detecting at least one detected identification element and is arranged to wirelessly transmit information about the item identified by the detected identification element to outside of the sterilization container.

The retainer systems already known from the prior art have several disadvantages. On the one hand, the individual retainer systems cannot communicate with each other, each retainer system requires complete sensor and communication electronics as well as an independent antenna, and on the other hand, a control unit/electronic unit is required for each retainer system.

SUMMARY

Therefore, the object of the present disclosure is to provide a system which eliminates or at least improves the disadvantages of the prior art. Furthermore, it is an object of the invention, in particular in the case of a high number of units, to reduce the manufacturing costs.

Accordingly, the present disclosure relates to a modular detection system for insertion into a sieve basket for detecting, monitoring and tracing sterile goods, in particular surgical instruments and/or motor systems and/or medical products in a sterilization cycle. The modular detection system is provided and configured as a sieve-basket insert, which can be inserted into the sieve basket directly or arranged on a base plate. The modular detection system is provided and configured with the following modules which can be individually and optionally electrically coupled:

a central electronic unit, which in particular is configured with at least one sensor, an energy storage unit, a data processing unit, and a writing and reading unit, preferably via NFC, (defined) number of slots for connecting and/or coupling a (predetermined) number of retainer systems, which are provided and configured for retaining sterile goods and each with at least one antenna system for reading a transponder, preferably an NFC transponder, of the sterile goods, and a (fixed) number of conducting tracks, in particular data lines and antenna lines and/or connections, which are provided and configured to electrically connect the slots and/or retainer systems to each other and/or to the central electronic unit.

In other words, the present disclosure relates to a modular sterile goods detection system prepared for insertion into a sieve basket for a sterilization cycle, comprising the following individually and optionally electrically couplable modules:

a central electronic unit, an electrical line assembly connectable to the electronic unit and having a number of free connection terminals/slots, and a number of, preferably differently dimensioned, sterile goods retainers/supports for individually holding sterile goods, each provided with at least one connection compatible with the free connection terminal and at least one antenna unit, wherein the at least one antenna unit is electrically connected to the at least one connection via a sterilization retainer/support internal line/conducting track.

In general, the present disclosure provides for a modular connection of multiple antenna systems to a central electronic unit. Here, the entire detection system is configured to function as an insert for a sieve basket and can be either directly mounted there or implemented via a removable insert. One advantage of such an insert or, respectively, the use of a base plate with data lines and antenna lines and individual retainer systems is that the production of specially adapted printed circuit boards is not necessary.

In other words, the module of the central electronic unit/control unit preferably has an energy source, preferably a rechargeable energy storage device, a data processing unit, a communication module, preferably a Bluetooth or WiFi communication module or other radio technologies, and an RFID reader or preferably an NFC reader, optionally with write function. The module of the conducting tracks, preferably data connections and antenna connections, preferably has a fixed number of conducting tracks connected/connectable to the data connection unit and the antenna interfaces of the central electronic unit. The individual conducting tracks terminate in a preferably fixed number of contact points forming slots which are provided for receiving at least one retainer system. The module of the individual retainer systems is understood to mean retainers which are adapted to different sterile goods, in particular instruments and/or motor systems and/or medical products, and have a simple sensor system, preferably with an energy storage device and a simple data processing unit. Furthermore, the at least one retainer system has at least one data and antenna interface. For reading RFID or preferably NFC transponders, which are provided in the individual sterile goods, the at least one retainer system has an antenna system, which has one or more antennas, which are connected to the central electronic unit either directly or via a (further) multiplexer.

Accordingly, it is possible to provide a system whose multiple antenna systems can be connected to a single/exactly one central control unit/electronic unit. Thus, individual retainer/support systems can be equipped with minimized electronics. Minimized electronics means that the retainer systems are equipped with simple sensors, in particular temperature, pressure, humidity, vibration, inclination, motion and PH value sensors and a rechargeable energy source/energy storage unit. This allows process steps, in particular sterilization process steps, sterilization times, and other sterile goods cycle parameters to be detected and the sensor values to be temporarily stored. Here, if possible, complete monitoring of the sterile goods cycle is an objective of the present disclosure. Accordingly, the implementation of a basic sensor system in the instrument retainer or instrument retainers, which is/are provided and configured to be able to detect and to temporarily store data, is advantageous. A complete sterilization cycle includes, but is not limited to, the following phases/process steps:

ultrasonic cleaning or manual pre-cleaning;

cleaning in the WD (washer-disinfector);

maintenance (for example, an oil spraying); and sterilization.

It is provided, if in the central electronic unit, at least one distribution module/multiplexer is provided and configured to drive at least two retainer systems via the respective antenna system, wherein each distribution module is configured to communicate via analog and digital inputs. A distribution module or multiplexer is a selection circuit in analog and digital electronics that can be used to select from a number of input signals and pass them through to the output. This enables multiple antenna systems, wherein each antenna system may have one or more antennas, to be connected to and to communicate with the central electronic unit. The distribution module has antenna interfaces and thus represents the contact/connection between the central electronic unit and the antenna connections and data connections or the conducting tracks with the connected antennas or antenna systems of the retainer system or retainer systems. By using such a distribution module, a large number of antennas can be driven without having to accommodate a large number of lines in the sieve basket.

Furthermore, it is preferred if multiple distribution modules are provided and configured in such a way that they are connected/connectable in series with the central electronic unit in order to control the respective distribution modules in series and thus to switch through the at least one respective antenna system in order to read out the sterile goods lying on the at least one respective antenna system.

Preferably, the at least one respective antenna system of the predetermined number of retainer systems is provided and configured as an NFC antenna. The use of an NFC antenna has the advantage that a direct proximity of the sterile goods to the antenna is necessary, and thus the error rate or a false inventory is lower/less likely. Alternatively, the use of an RFID antenna is also possible.

In an advantageous embodiment of the invention, it is provided that for the predetermined number of retainer systems, each is provided and configured with a sensor system for detecting and temporarily storing data, wherein the sensor system has at least one sensor, a data processing unit, a communication unit, a temporary memory, and a rechargeable energy storage unit. A temporary memory is a memory that stores data/information or similar things for a limited period of time, which are to be further processed by the same or another program. In this case, process steps and sensor values detected by the sensor system are temporarily stored and are transmitted to the central electronic unit as soon as the respective retainer system is connected to the central electronic unit. In parallel with the data exchange, it is preferably provided that the energy storage unit is charged.

It is preferred if the central electronic unit is provided and configured for detecting and temporarily storing data and is in communicative connection with the sensor system of the predetermined number of retainer systems and/or with the sterile goods held in the predetermined number of retainer systems.

It is advantageous if the data processing unit is provided and adapted to detect and write data to the predetermined number of retainer systems and/or to the sterile goods held by the predetermined number of retainer systems.

In other words, the data processing unit can write and temporarily store determined cleaning information/data, which is detected, for example, via the environment, in a data memory of the retainer device or, respectively, in an RFID tag of the sterile goods held by the retainer system. Therefore, there is a communication connection with the data processing unit, which has an internal data memory, so that the data processing unit can write the cycle information of the sterile goods cycle into the internal data memory of the retainer device or of the sterile goods, respectively, after processing the output signals. This has the advantage that the electronic unit is provided as a buffer/temporary memory, e.g. to temporarily store data when the corresponding retainer device or sterile goods for this data is not available. The detection system is then enabled to write the data to the corresponding retainer device or the corresponding sterile goods at a later point in time, when the corresponding retainer device or the corresponding sterile goods is/are available again. In this way, it is possible to move away from a permanent network connection or cloud solution, respectively.

In summary, the use of one respective sensor system in the retainer systems makes it possible to detect process steps without having to connect the entire electronic unit. This has the advantage that individual cleaning is also possible.

Advantageously, it is also provided, if the modular detection system is provided and configured to communicate and exchange data with at least one further modular detection system. In this way, it is possible that at least two independent modular detection systems, each with a central electronic unit, communicate with each other via these central electronic units and exchange data with each other. This is preferably done via a proprietary protocol, optionally via any radio technology. Thus, an entire mesh/network of modular detection systems or respectively of the respective electronic units of the modular detection systems can be built up, a so-called independent company mesh/network, which offers full information transparency. A proprietary protocol is a protocol that severely restricts the right and possibility of reuse and continued use as well as modification and adaptation by users and third parties.

Furthermore, it is preferred if the central electronic unit is provided and configured to read out, via the at least one distribution module/multiplexer, the at least one respective antenna system of the fixed number of retainer systems and to transmit the received data and/or information to an external unit, preferably a smartphone and/or an app and/or a control device, which is provided and configured to visually output the received data and/or information, preferably item number, serial number, antenna location, position and/or processing cycles.

Furthermore, it is advantageous if the installed electronics are protected against temperature and against cleaning agents, in particular moisture and alkaline cleaners. Here, a simple housing with insulation/isolation to bridge the high-temperature phase>130° C. for about 10 minutes in the sterilizer is fundamental. Such protection can be achieved by thick insulation layers in the housing as well as coatings on the electronics themselves. Encapsulation of the electronics is also conceivable.

Furthermore, the present invention relates to a retainer system for retaining sterile goods, in particular surgical instruments and/or motor systems and/or medical products. In this regard, it is provided that the retainer system comprises a sensor system for autonomously detecting process steps, wherein the retainer system is provided and configured to be connected to a modular detection system according to one of the preceding aspects.

Furthermore, in other words, different retainer systems for instruments and motor systems can be placed on this insert for the sieve basket, which are connected to the existing interfaces. These retainer systems in turn have implemented NFC antennas with which NFC transponders on the medical products/sterile goods can be read. Furthermore, there is a sensor unit/sensor system in each of the retainer systems, which has a sensor, a data processing unit, a temporary memory, and a rechargeable energy storage device. If more than one antenna is used, the central electronic unit also contains at least one multiplexer.

Furthermore, the present invention relates to a sieve basket system for monitoring and tracing sterile goods, in particular surgical instruments and/or motor systems and/or medical products, in a complete sterile goods cycle. Accordingly, it is preferred if a first and at least one further sieve basket are provided and configured in a stacked/stackable manner, into each of which a modular detection system according to one of the preceding aspects is inserted/insertable, wherein only the modular detection system of the first sieve basket comprises the central electronic unit, which is connected/connectable to the modular detection system of the at least one further sieve basket without the module of the central electronic unit, preferably via further distribution modules/multiplexers.

In other words, several sieves/sieve baskets, which are always provided together in a composite manner, can be stacked. Here, however, it is provided that only the first sieve basket, which is also referred to as the main sieve, contains the central electronic unit. The connection to the other sieves/sieve baskets and their antennas or antenna systems can then be established via contacts/interfaces and distribution modules.

Furthermore, the present invention relates to a method for monitoring a sterile goods cycle using at least one modular detection system according to one of the preceding aspects, comprising the following steps:

detecting and temporarily storing process steps and/or sensor values of at least one retainer system;

connecting/coupling the at least one retainer system to the central electronic unit of the modular detection system via at least one data and antenna interface;

transmitting data, in particular process steps and sensor values, of the at least one retainer system to the data processing unit of the modular detection system;

charging the energy storage unit;

analyzing and evaluating the data in the data processing unit of the modular detection system;

reading out an instrument ID for matching with a stored
list for the at least one connected/coupled retainer
system; and outputting information in case of a negative matching
result.

In other words, once the at least one retainer system is
connected to the central electronic unit, the collected data is
transmitted and the energy storage device is charged. Sub-
sequently, the data is further analyzed and evaluated with an
efficient data processing unit. Here, another object is to
check the correct instrument placements. This is done by
reading out the individual instruments placed in the retainer
systems or the retainer system, respectively.

In summary, the invention relates to an insert for a sieve
basket that has a central electronic unit that has sensors,
energy storage devices, communication modules, and an
NFC writing/reading unit. Furthermore, the insert has data
connections and antenna connections leading to a defined
number of slots to which intelligent/smart retainer systems
are selectively connected, each having NFC antennas. In
addition, the individual retainer systems have a simple
sensor unit that can temporarily store and pass on data. Thus,
the sieve/sieve basket and its sterile goods/product can be
inventoried in real time and is interactive through real-time
recognition. The corresponding sterile goods/product with
serial number and service life can be reported back to the
user immediately. Removal of the sterile goods/product is
thus detected and logged/recorded accordingly.

The system uses the existing sensors to monitor the
environment and automatically detects whether ultrasonic
cleaning, cleaning in the WD, maintenance, such as oil
spraying, or sterilization is being performed. In this case, it
is possible to extend the range of further sensor systems. In
the event that a retainer system is disconnected from the
sieve basket, the sensor unit installed in the retainer system
stores the data and passes them on to the central electronic
unit in the sieve basket after reconnection so that an evalu-
ation can take place. Furthermore, it is possible to check at
any time whether an instrument has been placed in the
correct retainer system, and to do this in real time. For this
purpose, the transponders installed in the sterile goods are
read and compared with a stored list. The retainer system is
identified by the installed data processing unit. The evalu-
ation can either be performed by the central data processing
unit or via Bluetooth, WiFi or any other radio standard, and
can be sent to an external computing unit and evaluated.

BRIEF DESCRIPTION OF THE DRAWINGS

FIG. 17 is an illustration showing the system structure of
the modular detection module with multiple distribution
modules according to the present disclosure;

FIG. 18 is an illustration showing communication
between two simple system structures of the modular detec-
tion module each having a distribution module according to
the present disclosure;

FIG. 19 is an illustration showing the mesh network
compared to a conventional network according to the pres-
ent disclosure;

DETAILED DESCRIPTION

Preferred configuration examples of the present disclo-
sure are described below based on the accompanying fig-
ures.

Figures 1, 2, 3, 4, 5, 6:
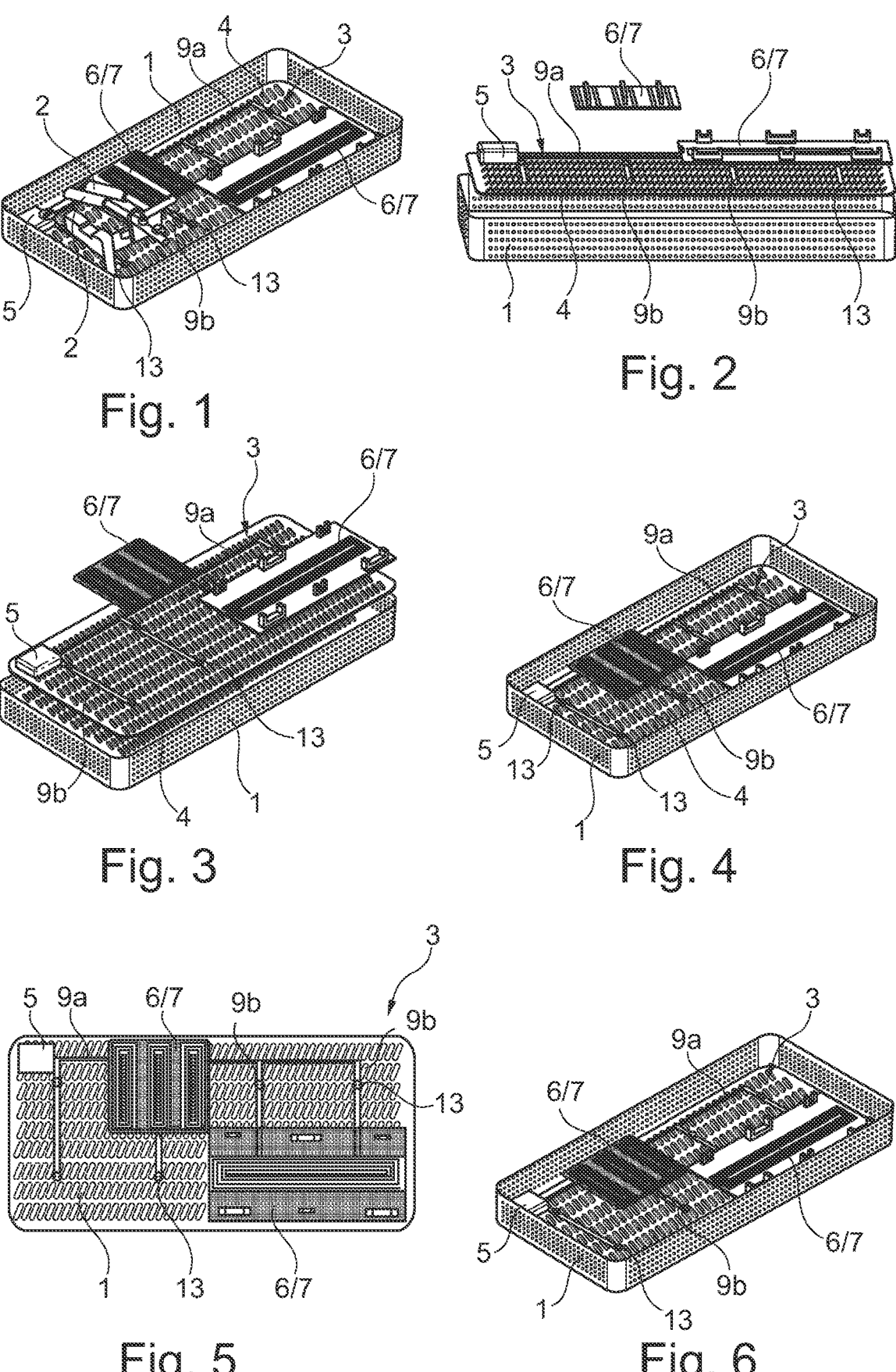
FIG. 1 is an illustration showing a modular detection
system according to the present disclosure.
FIG. 2 is an exploded side view of the modular detection
system according to the present disclosure.
FIG. 3 is a further exploded view of the modular detection
system according to the present disclosure.
FIG. 4 is an illustration showing the sieve basket with the
modular detection module according to the present disclo-
sure arranged on a base plate.
FIG. 5 is an illustration showing the modular detection
module according to the present disclosure arranged on a
base plate.
FIG. 6 is an illustration showing the modular detection
module according to the present disclosure directly inserted
into the sieve basket.

FIG. 1 is an illustration showing a modular detection
system according to a first configuration example of the
present disclosure. FIG. 1 shows the modular detection
system for insertion into a sieve basket 1 for detecting,
monitoring and tracing sterile goods 2. The modular detec-
tion system is provided and configured as a sieve-basket
insert 3, which is insertable into the sieve basket 1, accord-
ing to a second configuration example (see FIGS. 5 and 6),
directly or, according to a first configuration example (see
FIGS. 1 to 4), arranged on a base plate 4. FIG. 1 shows a
central electronic unit 5, a defined number of slots 6, a
predetermined number of retainer systems 7 (here two
retainer systems) and a defined number of conducting tracks
9.

In FIG. 1 it is shown that the base plate 3, which
preferably has the same size and shape as the base area of the
sieve basket 1, is inserted/insertable into the sieve basket 1.
On the base plate 3, the central electronic unit 5 is arranged,
which is connected to the conducting tracks 9, which in turn
are connectable/connected via at least one antenna connection and data connection 13 to at least one plate-shaped/board-shaped retainer system 7. FIGS. 2 and 3 show corresponding exploded views of FIG. 1, and FIG. 4 corresponds substantially to FIG. 1 without the sterile goods 2. Thus, FIGS. 2 to 4 will not be described further.

Figure 8:
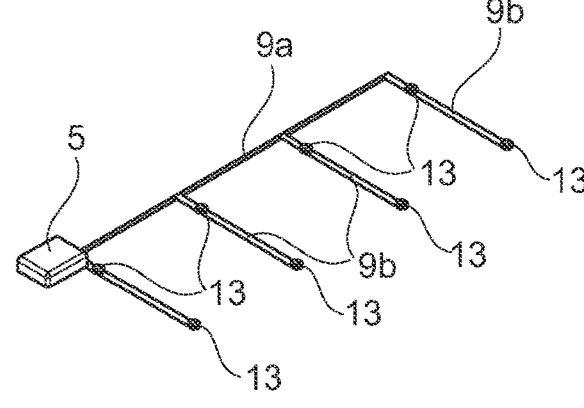
FIG. 8 is an illustration showing the modular detection
module comprising a central electronic unit and conducting
tracks according to the present disclosure.
Figure 9:
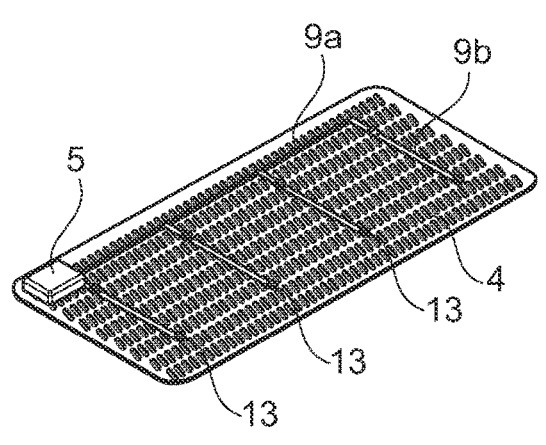
FIG. 9 is an illustration showing the modular detection
module consisting of a central electronic unit and the
conducting tracks arranged on the base plate according to
the present disclosure.

FIG. 1 shows in conjunction with FIGS. 8 and 9 the conducting tracks 9 in connection with the central electronic unit 5, which are preferably intended to have the conducting track structure shown in the Figures. It is provided that the conducting tracks 9*b* branch off at right angles from a conducting track 9*a* directly connected to the central electronic unit 5. Each conducting track 9*b* ends in an antenna connection and data connection 13, wherein it is further preferred that at least one further antenna connection and data connection 13 is provided on a conducting track 9*b*. Furthermore, it is preferred that exactly four conducting tracks 9*b* branching off from the conducting track 9*a* are provided, wherein fewer or more conducting tracks 9*b* may also be provided.

FIG. 1 shows in connection with FIGS. 11 to 14 the retainer systems 7 which are attached to the slots 6, wherein the slots are defined by the required number of antenna connections and data connections 13 depending on the retainer system 7. According to the present configuration examples, two differently configured retainer systems 7 are provided in the sieve basket 1, wherein each retainer system 7 is configured with a sensor unit 11, in which data and sensor values are detected and temporarily stored and which are transmitted to the central electronic unit 5 after connection to the latter.

Figure 11:
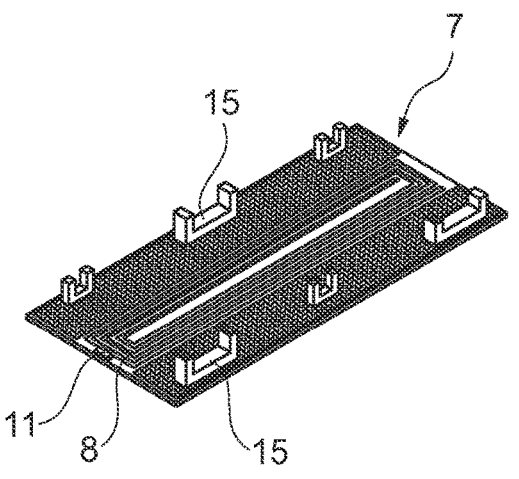
FIG. 11 is an illustration showing a retainer system with
an antenna according to the present disclosure.
Figure 12:
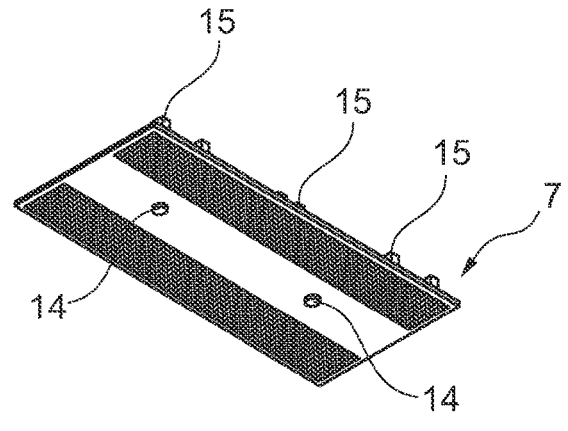
FIG. 12 is an illustration showing the underside of the
retainer system with an antenna and two antenna connec-
tions according to the present disclosure.

According to FIGS. 11 and 12, a retainer system 7 is provided, which is formed with an antenna system 8 consisting of an antenna.

Figures 13, 14, 15, 16:
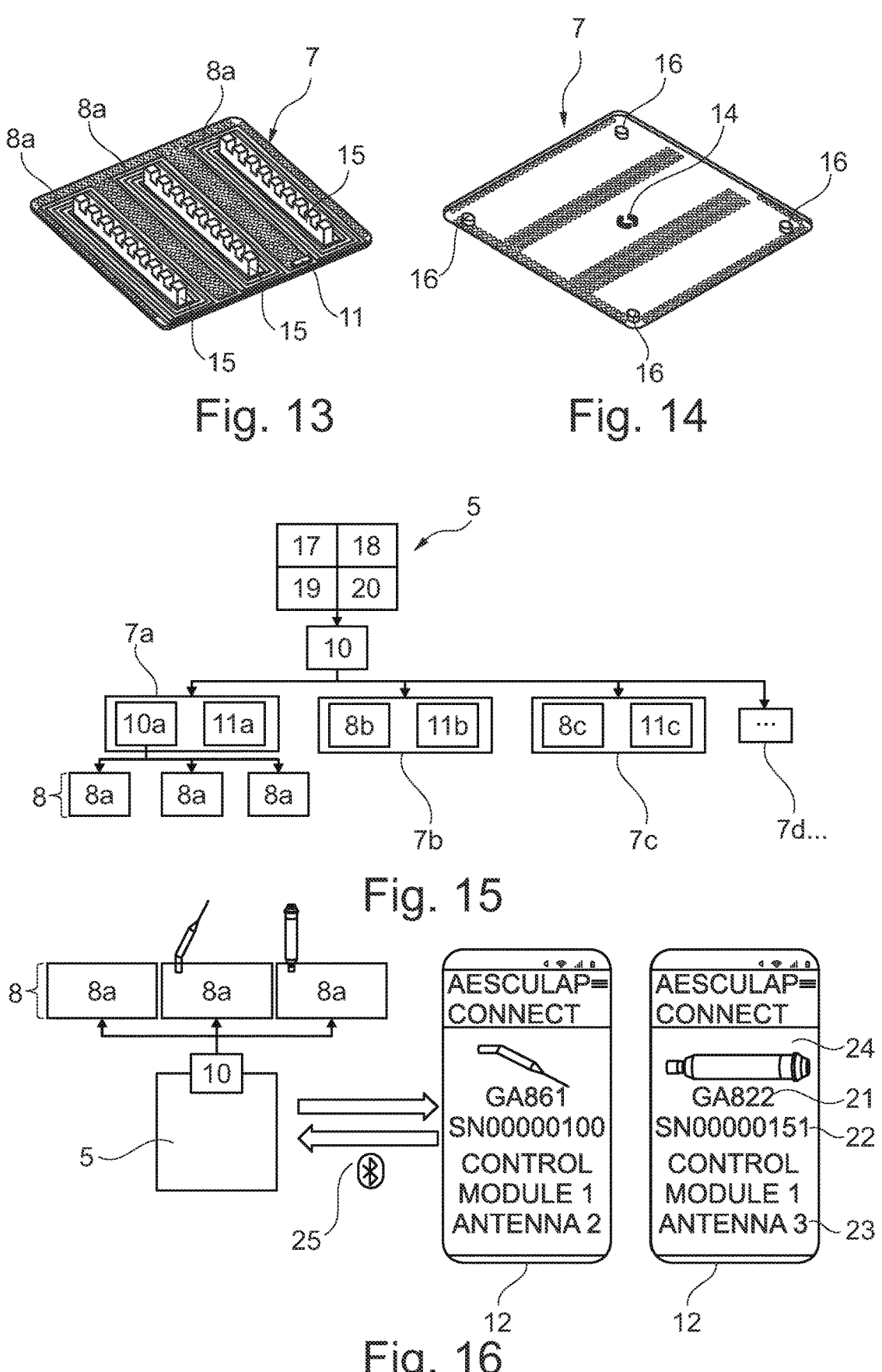
FIG. 13 is an illustration showing a retainer system with
an antenna system according to the present disclosure.
FIG. 14 is an illustration showing the underside of the
retainer system with an antenna system and an antenna
connection according to the present disclosure.
FIG. 15 is an illustration showing a system structure of the
modular detection module according to the present disclo-
sure.
FIG. 16 is an illustration showing a simple system struc-
ture of the modular detection module with a distribution
module and at least one external unit according to the
present disclosure.

FIG. 11 shows an upper side of such a board-like retainer system 7, on which at least one sterile goods bearing (base/clamp) 15 is formed/arranged, into which the sterile goods 2 can be inserted according to FIG. 1. FIG. 12 shows an underside of such a retainer system 7, in which the antenna connections 14 compatible with the antenna connections and data connections 13 of the conducting tracks 9, a so-called double connection, are shown. Via this, the retainer systems 7 can be attached to or fastened on the conductor structure to an antenna connection 14 (see FIGS. 12 and 14) compatible with an antenna connection and data connection 13. In FIG. 14 it is further shown that on the underside of the retainer system 7, in addition to the antenna connections 14, a bearing means 16 is provided at each corner, which is intended to be placed on and preferably fastened to the base plate 3 or the sieve basket 1, respectively.

According to FIG. 13, a retainer system 7 is provided with an antenna system 8 formed with three antennas 8*a*. The retainer system 7 also has a sensor unit 11, which is formed with a distribution module 10 (not shown) in order to address each of the three antennas 8*a*.

Figure 7:
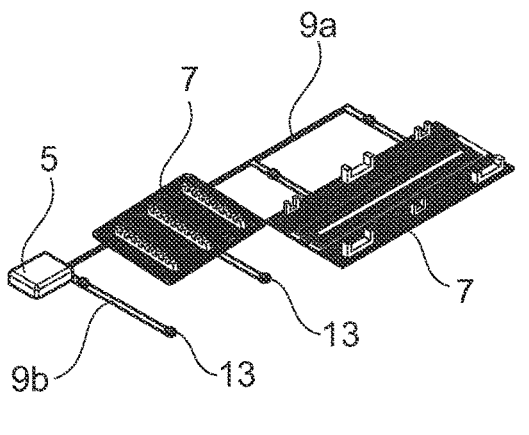
FIG. 7 is an illustration showing the modular detection
module according to the present disclosure.

FIGS. 5 to 7 are an illustration showing the modular detection module according to the second configuration example without base plate 3 and otherwise essentially corresponds to the structure of the first configuration example described above. A repeated description is therefore dispensed with at this point.

Figure 10:
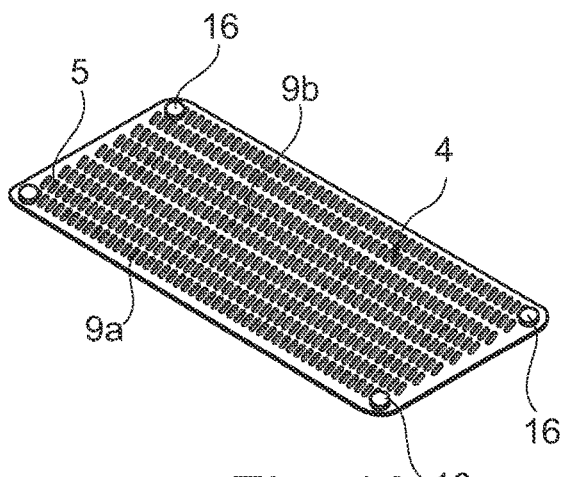
FIG. 10 is an illustration showing the underside of the
modular detection module arranged on the base plate con-
sisting of a central electronic unit and conducting tracks
according to the present disclosure.

FIGS. 9 and 10 are an illustration showing the top and bottom of the modular detection module arranged on the base plate 3, consisting of a central electronic unit 5 and the conducting tracks 9 according to the present disclosure. In FIG. 10, it is furthermore shown that further bearing means (spacers/latching feet/etc.) 16 are provided on the underside of the base plate 3 for insertion and preferably for fastening in the sieve basket(s) 1.

FIG. 15 is an illustration showing a system structure of the modular detection module according to the present disclosure. In FIG. 5, the central electronic unit 5 is shown in which an energy storage unit 17, a data processing unit 18, a communication module 19 and a reading unit 20 are provided. The central electronic unit 5 is connected to multiple retainer systems 7 via a distribution module 10. Here, the first retainer system 7*a* has a sensor system 11*a* and an additional distribution module 10*a* which is connected to an antenna system 8, wherein the antenna system 8 consists of multiple antennas 8*a*, each of which is addressed by the distribution module 10*a*. Furthermore, a second retainer system 7*b* and a third retainer system 7*c* are provided, which each have an antenna system with several antennas 8*b* or 8*c* and a sensor unit 11*b* or 11*c*, respectively, and are each addressed by the first distribution module 10. The number of retainer systems 7 as well as the antenna systems or antennas 8 can be expanded as desired in a modular way.

FIG. 16 is an illustration showing a simple system structure of the modular detection module with a distribution module 10 and at least one external unit 12 according to the present disclosure. Here, the central electronic unit 5 controls the respective antennas 8*a* of the antenna system 8 via a distribution module 10 and reads them out. This information is further communicated to an external unit 12. In the case shown, the external unit 12 is an app on a smartphone that visually outputs the information about item number 21, serial number 22, antenna location 23 or respectively storage location on a display 24. Further data such as processing cycles etc. may be displayed additionally. A preferred transmission means, preferably configured bidirectionally, is in this case Bluetooth or respectively any other radio standard.

FIG. 17 is an illustration showing the system structure of the modular detection module with multiple distribution modules 10 according to the present disclosure. FIG. 17 shows the central electronic unit 5 which controls the three distribution modules 10*a*, 10*b* and 10*c* in series. Each distribution module 10*a*, 10*b* and 10*c* in turn switches through an antenna system 8 with the respective three antennas 8*a*, three antennas 8*b*, and three antennas 8*c*. This outputs which sterile goods 2 (medical products or instruments and/or motor systems) are located on each of the three antennas 8*a*, each of the three antennas 8*b* and each of the three antennas 8*c*. In this way, very complex sieves/sieve baskets 1 can be inventoried. Here, it is particularly preferable to benefit from the immediate proximity of the tags to the antenna and thus prevent incorrect inventorying.

FIG. 18 is an illustration showing the communication between two simple system structures of the modular detection module with one distribution module 10 each according to the present disclosure. FIG. 18 shows two central electronic units 5*a* and 5*b*, which can communicate with each other/among each other and exchange data via the transmission means 25, preferably via Bluetooth. The central electronic units 5*a* and 5*b* each have a distribution module 10, which in turn addresses/drives an antenna system 8 with three antennas 8*a* and 8*b* in each case.

FIG. 19 is an illustration showing the mesh network according to the present disclosure in comparison with a conventional network. On the right side of FIG. 19, a conventional network is shown in which all detection systems, referred to here simply as electronic units 5, converge at a central intermediary 26 and direct communication between the electronic units 5 is not provided. The left side of FIG. 19 shows a mesh network according to the present disclosure, in which direct communication between the electronic units 5 is possible and thus no intermediary is required.

Figure 20:
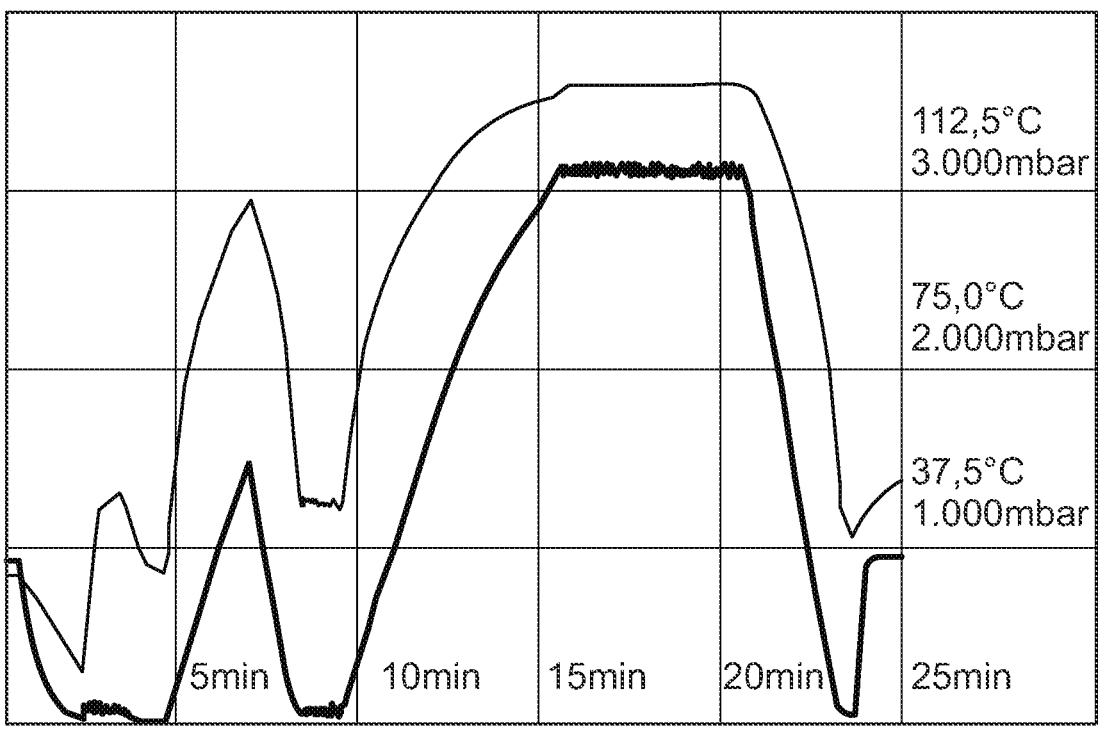
FIG. 20 is an illustration of an exemplary temperature and
pressure curve in a sterilizer according to the present dis-
closure.

FIG. 20 is a representation of an exemplary temperature and pressure curve in a sterilizer according to the present disclosure. Here, the upper curve represents the temperature curve (Y-axis) and the lower curve represents the pressure curve over time (x-axis) in a sterilizer.

The invention claimed is:

1. A modular detection system for insertion into a sieve basket for detecting, monitoring and tracing sterile goods, the modular detection system comprising:

a sieve-basket insert that is designed and configured to be inserted into the sieve basket directly or arranged on a base plate; and a plurality of modules comprising:

a central electronic unit;

a number of retainer systems that are configured for retaining sterile goods and that each include at least one antenna system for reading a transponder of the sterile goods, wherein each of the number of retainer systems comprises at least one antenna connection;

a number of slots that are defined or freely selectable for connecting and/or coupling sterile goods bearings of the number of retainer systems; and a number of conducting tracks, which are configured to electrically connect the number of slots and/or the number of retainer systems to each other and/or to the central electronic unit, wherein the number of conducting tracks each comprises at least one antenna connection and data connection compatible with the at least one antenna connection of the number of retainer systems, each of the plurality of modules being configured to be individually coupled.

2. The modular detection system according to claim 1 further comprising at least one distribution module in the central electronic unit, the at least one distribution module configured to drive at least two retainer systems via the respective antenna system.

3. The modular detection system according to claim 1, wherein multiple distribution modules are configured in such a way that they are connected/connectable in a series with the central electronic unit in order to drive the respective distribution modules in series and thus to switch through the at least one respective antenna system in order to read out the sterile goods lying on the at least one respective antenna system.

4. The modular detection system according to claim 1, wherein the at least one respective antenna system of the number of retainer systems is configured as an NFC antenna.

5. The modular detection system according to claim 1, wherein the number of retainer systems is each configured with a sensor system for detecting and temporarily storing data, wherein the sensor system has at least one sensor, a data processing unit, a temporary memory, and a rechargeable energy storage unit.

6. The modular detection system according to claim 5, wherein the central electronic unit is configured for detecting and temporarily storing data and is in communication with the sensor system of the number of retainer systems and/or with the sterile goods held in the number of retainer systems.

7. The modular detection system according to claim 5, wherein the data processing unit is adapted to detect and write data to the number of retainer systems and/or to the sterile goods held by the number of retainer systems.

8. The modular detection system according to claim 1, wherein the modular detection system is adapted to communicate and exchange data with at least a second detection system.

9. The modular detection system according to claim 2, wherein the central electronic unit is configured to read out data and/or information, via the at least one distribution module, the at least one respective antenna system of the number of retainer systems and to transmit the data and/or information to an external unit, which is configured to visually output the data and/or information.

10. A retainer system configured to be connected to the modular detection system according to claim 1, the retainer system comprising a sensor system for autonomously detecting process steps.

11. A sieve basket system for monitoring and tracing sterile goods in a sterile goods cycle, the sieve basket system comprising:

a first sieve basket;

a first modular detection system comprising:

a first sieve-basket insert that is designed and configured to be inserted into the first sieve basket directly or arranged on a first base plate; and a plurality of first modules comprising:

a central electronic unit;

a number of first slots that are defined or freely selectable for connecting and/or coupling a number of first retainer systems that are configured for retaining sterile goods and that each include at least one respective first antenna system for reading a respective transponder of each of the sterile goods; and a number of first conducting tracks, which are configured to electrically connect the number of first slots and/or the number of first retainer systems to each other and/or to the central electronic unit, each of the plurality of first modules being configured to be individually coupled;

a second sieve basket;

a second modular detection system comprising:

a second sieve-basket insert that is insertable into the second sieve basket directly or arranged on a second base plate; and a plurality of second modules comprising:

a number of second slots that are defined or freely selectable for connecting and/or coupling a number of second retainer systems that are configured for retaining sterile goods and that each include at least one respective second antenna system for reading a respective transponder of each of the sterile goods; and a number of second conducting tracks, which are configured to electrically connect the number of second slots and/or the number of second retainer systems to each other, each of the plurality of second modules being configured to be individually coupled, wherein the second modular detection system does not have a central electronic unit; and wherein the central electronic unit of the first modular detection system is designed and configured to be connected to the second modular detection system.

* * * * *